United States Patent [19]

Alpert

[11] Patent Number: 5,564,929
[45] Date of Patent: Oct. 15, 1996

[54] FLEXIBLE ROOT CANAL PROSTHESIS

[76] Inventor: Edward L. Alpert, 148 Scolfield Town Rd., Stamford, Conn. 06903

[21] Appl. No.: 291,616

[22] Filed: Aug. 17, 1994

[51] Int. Cl.⁶ .................................................. A61C 5/02
[52] U.S. Cl. ........................................... 433/224; 433/220
[58] Field of Search ................................. 433/224, 220, 433/102

[56] References Cited

U.S. PATENT DOCUMENTS

| | | | |
|---|---|---|---|
| 1,649,508 | 11/1927 | Carmichael | 433/224 |
| 4,490,116 | 12/1984 | Deutsch et al. | 433/215 |
| 4,576,081 | 3/1986 | Felthius et al. | 87/6 |
| 4,778,388 | 10/1988 | Yuda et al. | 433/221 |
| 4,936,776 | 6/1990 | Kwiatkowski | 433/220 |
| 4,952,150 | 8/1990 | Schiwiora et al. | 433/220 |
| 5,051,093 | 9/1991 | Fitzmorris | 433/224 |
| 5,098,304 | 3/1992 | Scharf | 433/215 |

FOREIGN PATENT DOCUMENTS

| | | | |
|---|---|---|---|
| 220491 | 8/1924 | United Kingdom | 433/224 |

*Primary Examiner*—Cary E. O'Connor
*Attorney, Agent, or Firm*—Dilworth & Barrese

[57] ABSTRACT

A flexible rope-like root canal prosthesis and method of use are provided for repair of a damaged tooth. The flexible rope-like root canal prosthesis is contacted with a stiffening agent to form a composite that is moldable to conform the interior of the root canal. The stiffened rope-like root canal prosthesis is bonded into the root canal and serves as a foundation for restoring the pulp cavity core and allowing for additional prosthesis to be applied to the tooth.

15 Claims, 3 Drawing Sheets

FLEXIBLE ROOT CANAL PROSTHESIS

BACKGROUND

1. Technical Field

In dentistry, root canal supports and fillers are used for repair of teeth. More particularly, a flexible rope-like root canal prosthesis is disclosed for use in connection with restoring the pulp cavity of a tooth and prosthetic dental implants.

2. Background of Related Art

Restoration and repair of damaged teeth and gums is a common occurrence in modern dentistry. Natural teeth are specially adapted to withstand the rugged environment of the mouth and the rigors and intense pressures of chewing. A normal tooth is composed of a crown, neck, root and pulp cavity. A longitudinal cross-section of a tooth shows a central chamber having the general form of the tooth. Processes of the chamber pass from its body, one for each root and down each root and open at the apex by the apical foramen.

Teeth may become damaged due to disease, infection and/or trauma. To prevent further damage and pain, the damaged tooth may be repaired by procedures which include removal of the pulp in the central chamber and root. The root is then cleaned and prepared for receiving the materials and prosthetics that form the basis of a restored tooth. In certain instances, the root canal must be drilled open and bored out to receive such prosthetics. Care must be taken to avoid removing too much material from within the root and weakening the remaining tooth wall. After preparing the canal, the root must be sealed with inert biocompatable fillers to prevent infection and continuing decay. Gutta percha is commonly used as such a filler.

When the natural crown has been damaged and is to be replaced with a prosthetic crown, one or more root canal posts may be placed within the root canal for support. The posts are cemented in the canal and serve as the foundation for the prosthetic crown. Root posts are ordinarily elongated cylindrical solid or cannulated bodies such as those described in U.S. Pat. No. 4,936,776 (castable translucent glass—ceramic or castable phosphate bound apatite containing compositions), U.S. Pat. No. 4,952,150 (sections of precious-metal alloys having differing ductilities or flexural rigidities which are bonded together by soldering, welding or sintering), U.S. Pat. No. 4,778,388 (root canal post of stainless steel, gold, silver, palladium alloys or ceramic having a shank, head and a bore axially through the head and shank), and U.S. Pat. No. 4,490,116 (dental post with self-tapping threading and relatively movable walls).

An ideal root canal post should be strong enough to withstand the rigors of the mouth and conform to the natural root canal chamber as closely as possible to avoid having to shape the canal to such a degree that the walls of the canal are weakened and brittle. Moreover, if the root canal chamber has been damaged or otherwise misshapen the above-described root canal posts would at best only provide minimal conformance to the required shape.

SUMMARY

A flexible root canal prosthesis is provided for use in filling a root canal and as support for tooth repair. The flexible root canal prosthesis is rope-like and may be woven fabric, non-woven fabric, yarn, cord or mesh.

In one aspect, a flexible rope-like root canal prothesis is contacted with a stiffening agent and allowed to stiffen. The stiffened rope-like root canal prosthesis is then inserted into the root canal, fixed in the root canal and the canal is sealed. In another aspect, the flexible rope-like root canal prosthesis is inserted into a root canal, bonded within the root canal, and the canal is sealed. In either aspect, the portion of the stiffened rope-like root canal prosthesis extending above the sealed root canal may then used as an anchor for filler and any suitable prosthesis over the root of the tooth.

DETAILED DESCRIPTION OF PREFERRED EMBODIMENTS

Flexible rope-like root canal prosthesis as described herein provides filler and support for a root canal that has been cleared of pulp and extraneous matter. For convenience, the flexible rope-like root canal prosthesis will be referred to as "rope", but it should be understood that, as described below, the prosthesis may take configurations other than a conventional corded rope. The unique properties of the flexible rope-like root canal prosthesis allow relatively minimal wall reduction of the root canal during preparation by virtue of the rope's ability to fit into and be conformed to the contour of the canal as compared to the relatively fixed and unyielding configurations of existing root canal posts. After the rope is stiffened and bonded, i.e., secured within the root canal, the stiff rope strengthens the root canal and provides an adequate support for any underlying or overlying filler for the pulp cavity. The ability of the rope to integrate the stiffening agent, cement, or luting agent allows the resulting prosthetic rope and interior fill of the root canal to have variable properties, e.g., elastic modulus, compressive strength, thermal coefficient, etc. to closely mimic such properties of the natural tooth structure or to be suitable for specific applications calling for increased or decreased strength, flexibility, etc.

Fibers which may be used in forming the rope are well-known in the art. Examples of such fibers are glass fibers, ceramic fibers, metal fibers, and polymeric fibers such as cellulose fibers, polyamide fibers, aramid fibers, polyester fibers, acrylic fibers, vinyl and modacrylic fibers, polyolefin fibers, polytetrafluroethylene fibers, carbon fibers and any combination or blend of the foregoing fibers. Especially preferred are etched fibers of glass or ceramic such as that described in U.S. Pat. No. 5,098,304, herein incorporated by reference. The fibers must be biocompatible, i.e., they do not cause adverse effects such as toxicity in vivo.

Figure 1:
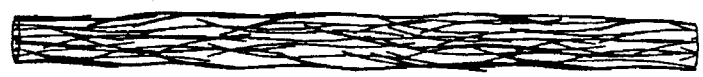
FIG. 1 illustrates an example of a flexible root canal prosthesis formed from non-woven fabric.
Figure 2:
FIG. 2 illustrates an example of a flexible root canal prosthesis formed from a mesh.
Figure 3:
FIG. 3 illustrates an example of a flexible root canal prosthesis formed from a woven fabric.
Figure 4:
FIG. 4 illustrates an example of a flexible root canal prosthesis formed from yarn.
Figure 5:
FIG. 5 illustrates another example of a flexible root canal prosthesis formed from corded fibers.

The configuration of fibers contained within the rope is variable and any configuration of rope known in the art may be used. Examples of such configurations include a non-woven configuration such as that shown in FIG. 1, a mesh configuration such as that shown in FIG. 2, a woven configuration such as that shown in FIG. 3, yarn configuration such as that shown in FIG. 4, or a corded configuration such as that shown in FIG. 5. The density of the yarn, weave, mesh, cord or non-woven fabric may be varied and to affect the flexibility and capillarity of the rope. By increasing the density, e.g., by tightening the weave or increasing the denier, etc., the rope may be made less flexible and/or less permeable to stiffening agent as described below.

The rope is contacted with a stiffening agent which reduces flexibility and creates a stiffened, strengthened rope that provides an adequate support to fill and strengthen the walls of a cored root canal. The portion of the stiffened rope which extends above the root canal area may be used as an anchor or foundation for any pulp cavity filler or any prosthesis prosthetic which contacts or overlays the root canal. Stiffening agents should penetrate into the rope and harden there. In this way, a composite matrix is created from dispersion of the stiffening agent through the interstitial spaces of the rope.

In one aspect, the stiffening agent is dissolved in solvent to form a mixture and the rope is contacted with the stiffening agent by dipping the rope into the mixture or by painting or spraying the mixture on the rope. The degree of incorporation of stiffening agent is determined by the density of the fibers, i.e., the more dense, the less penetration per unit time. Also affecting incorporation is the viscosity of the mixture, i.e., the more viscous, the less penetration per unit time. When the solvent evaporates, the stiffening agent is deposited in the interstices where a hard reinforcing medium is formed. Examples of suitable stiffening agents for solvent casting include polycarbonates, polyamides, polyacrylates, polyurethanes, polyethers and polyvinyls. Examples of suitable solvents include acetone, hexfluoroisopropanol, hexafluoroacetone sesquihydrate, trichloroethane, chloroform, creosol, benzene, methylene chloride and ketones. Other suitable solvents are well-known in the art.

In another aspect, the stiffening agent is a resin which polymerizes while or after the resin is wicked or otherwise made to penetrate the interstices of the rope. Such resins are well-known and examples include polyacrylates such as polymethyl methacrylate, polyethyl methacrylate; polyacrylonitriles; polyamides; polyesters such as alkyds, unsaturated polyesters, aromatic polyesters, aromatic polycarbonates and polydiallyl esters; polyethers such as epoxy resins, phenoxy resins, and polyphenylene oxide resins; polyfluoroolefins; polyolefins such as polyethylene and polypropylene; polystyrene; polysulfones; polyurethanes; and polyvinyls such as polyvinyl carbazole, polyvinyl chloride and polyvinyl fluoride. It should be noted that, when appropriate, any of the foregoing stiffening agents may be solvent cast to evaporate and form the hard reinforcing medium.

Figure 6:
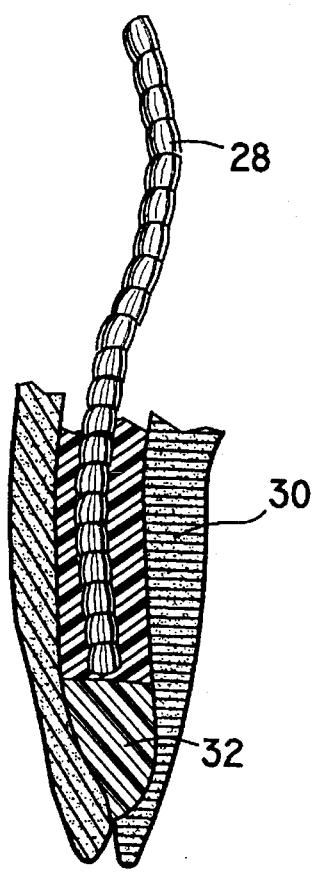
FIG. 6 illustrates a flexible root canal prosthesis inserted into a root canal.
Figure 7:
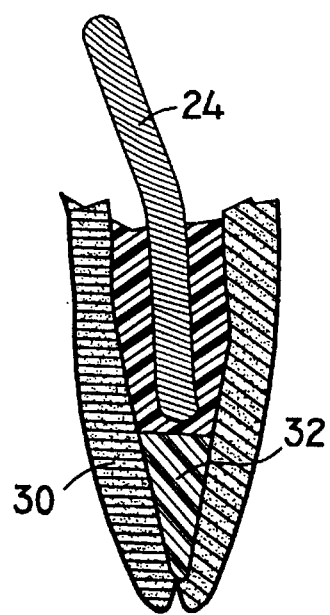
FIG. 7 illustrates another flexible root canal prosthesis inserted into a root canal.

In a preferred embodiment, after the root canal is prepared and cleaned, the rope is contacted with the stiffening agent which is allowed to diffuse or be wicked into the rope. When the rope begins to stiffen, it is shaped by hand or otherwise to fit the contour of the open root canal. Prior to inserting the rope, a luting agent may be applied to the interior walls of the root canal. Any well-known luting agent is appropriate as long as it does not adversely react with the rope or stiffening agent. The partially or completely stiffened rope is then inserted to an appropriate depth in the root canal. FIG. 6 illustrates the cord rope 28 of FIG. 5 inserted in the root 30. A filler 32 such as gutta percha seals the apical portion of the root 30. FIG. 7 illustrates the woven rope 24 of FIG. 4 inserted in root 30. As above, a filler 32 seals the apical portion.

Figure 8:
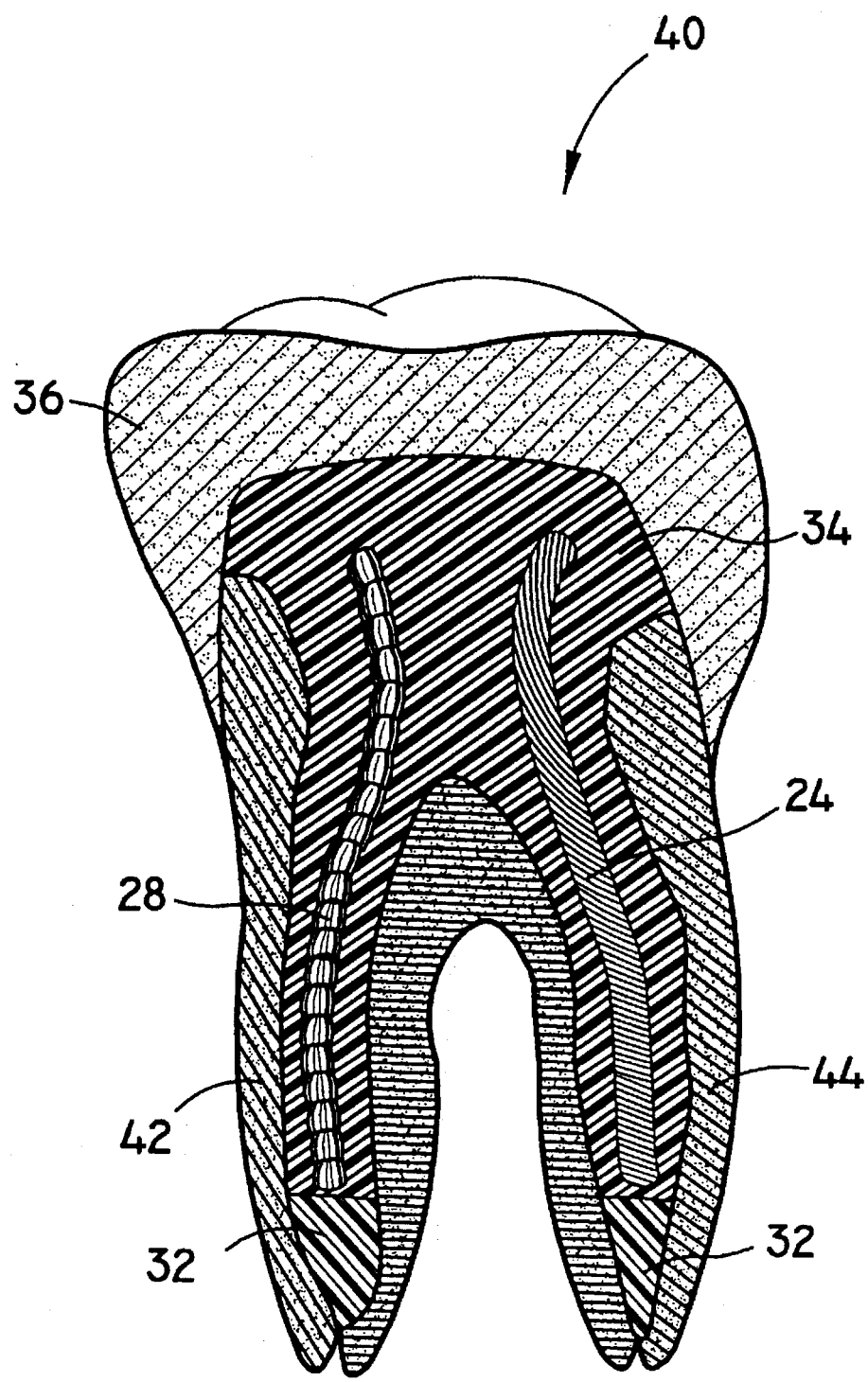
FIG. 8 illustrates two flexible root canal prostheses inserted into root canals and surrounded by dental prosthetics.

Any conventional filler, e.g., plastic material, for use in tooth restoration may then be applied to the root canal and around the rope to fill any remaining space and be allowed to harden. Such plastic materials are well-known and examples include composite resin, glass isomer cement and amalgam. After the plastic material hardens and bonds the stiffened rope within the root canal, the crown portion of the tooth may be built up by additional plastic material. FIG. 8 illustrates a repaired tooth 40. Root portions 42 and 44 have cord rope 28 and woven rope 24, contained within their respective canals. Plastic material 34 surrounds the ropes and supports the prosthetic crown 36.

In another aspect, a rope is inserted into the root canal and the stiffening agent and plastic material (which can be one and the same) are applied in the tooth. The stiffening agent penetrates and is wicked along the length of the rope. The rope is allowed to stiffen and the tooth repair is completed as described above.

It will be understood that various modifications may be made to the embodiments disclosed herein. For example, the rope has been exemplified as elongated and generally cylindrical in FIGS. 1, 3, 4 and 5 but it is contemplated that any elongated shape of varied cross section such as a ribbon may be used. It is also contemplated that combinations of the above-mentioned fibers may be used in connection with combinations of the above described configurations, e.g., a metal fiber extending the length of the rope and surrounded by woven, non-woven, yarn and/or corded glass, ceramic etc. fibers. Therefore the above description should not be construed as limiting, but merely as exemplifications of preferred embodiments. Those skilled in the art will envision other modifications within the scope and spirit of the following claims.

What is claimed is:

1. A method for restoring the root canal of a tooth comprising:

preparing the root canal;

providing a flexible rope-like root canal prosthesis;

contacting the flexible rope-like root canal prosthesis with a stiffening agent;

allowing the flexible rope-like root canal prosthesis to at least partially stiffen;

inserting the at least partially stiffened flexible rope-like root canal prosthesis into the root canal; and sealing the root canal.

2. A method according to claim 1 wherein the flexible rope-like root canal prosthesis is fabricated from a fiber selected from the group consisting of ceramic fibers, glass fibers, polymeric fibers, metal fibers, carbon fibers and combinations thereof.

3. A method according to claim 1 wherein the flexible rope-like root canal prosthesis is in the form of a configuration selected from the group consisting of mesh, non-woven fabric, woven fabric, cord and yarn.

4. A method according to claim 1 further comprising adding a luting agent into the root canal.

5. A method according to claim 1 wherein the stiffening agent is selected from the group consisting of polyacrylates, polyurethanes, polyethers, polyesters, polyfluoroolefins, polyolefins, polystyrene, and polyvinyls.

6. A method according to claim 1 further comprising bending the stiffened flexible rope-like root canal prosthesis to a shape which approximates the shape of the area within the root canal that receives the stiffened flexible rope-like root canal prosthesis.

7. A method for restoring the root canal of a tooth comprising:

provide a flexible rope-like root canal prosthesis;

inserting the flexible rope-like root canal prosthesis into the root canal;

bonding the flexible rope-like root canal prosthesis within the root canal; and sealing the root canal.

8. A method according to claim 7 wherein the flexible rope-like root canal prosthesis is fabricated from a fiber selected from the group consisting of ceramic fibers, glass fibers, polymeric fibers, metal fibers, carbon fibers and combinations thereof.

9. A method according to claim 7 wherein the flexible rope-like root canal prosthesis is in the form of a configuration selected from the group consisting of mesh, nonwoven fabric, woven fabric, cord and yarn.

10. A method according to claim 7 further comprising contacting a stiffening agent with the flexible rope-like root canal prothesis within the root canal.

11. A method according to claim 10 wherein the stiffening agent is selected from the group consisting of polyacrylates, polyurethanes, polyethers, polyesters, polyfluoroolefins, polyolefins, polystyrene, and polyvinyls.

12. A method according to claim 7 further comprising contacting a stiffening agent with the flexible rope-like root canal prosthesis prior to inserting the flexible rope-like root canal prosthesis into the root canal.

13. A method according to claim 12 wherein the stiffening agent is selected from the group consisting of polyacrylates, polyurethanes, polyethers, polyesters, polyfluoroolefins, polyolefins, polystyrene, and polyvinyls.

14. A method according to claim 7 further comprising adding a luting agent to the root canal.

15. A method according to claim 7 further comprising building a foundation for a prosthetic crown around the flexible rope-like root canal prosthesis and adhering a prosthetic crown to the foundation.

\* \* \* \* \*